US009746420B2

(12) United States Patent
Bouzid

(10) Patent No.: US 9,746,420 B2
(45) Date of Patent: *Aug. 29, 2017

(54) DIFFERENTIAL SCAN IMAGING SYSTEMS AND METHODS

(71) Applicant: LI-COR, Inc., Lincoln, NE (US)

(72) Inventor: Ahmed Bouzid, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,085

(22) Filed: Sep. 14, 2015

(65) Prior Publication Data
US 2016/0003739 A1    Jan. 7, 2016

Related U.S. Application Data

(63) Continuation of application No. 13/084,371, filed on Apr. 11, 2011, now Pat. No. 9,134,241.

(51) Int. Cl.
*G01N 21/64* (2006.01)
*G02B 21/16* (2006.01)
*G01N 21/17* (2006.01)

(52) U.S. Cl.
CPC ......... *G01N 21/6456* (2013.01); *G02B 21/16* (2013.01); *G01N 2021/1785* (2013.01)

(58) Field of Classification Search
CPC ....... G01N 21/6456; G01N 2021/1785; G02B 21/16

(Continued)

(56) References Cited

U.S. PATENT DOCUMENTS 5,827,190 A  * 10/1998 Palcic ............... A61B 1/043
                                                600/109
6,495,812 B1   12/2002 Wurm et al.
(Continued)

FOREIGN PATENT DOCUMENTS

JP        2008203138      9/2008
WO    WO 2010084381 A1    7/2010

OTHER PUBLICATIONS

Christensen et al. "Optical System Design for Biosensors Based on CCD Detection". Biosensors and Biodetection: Methods in Molecular Biology, vol. 503, 2009, pp. 239-258.*

(Continued)

*Primary Examiner* — Zhihan Zhou
(74) *Attorney, Agent, or Firm* — Leydig, Voit & Mayer, LTD; Gerald T. Gray

(57) ABSTRACT

Systems and methods for producing background-reduced fluorescence imaging signals include an illumination system that provides illumination light from an illumination source to a targeted area on the sample platform, a sensor adapted to detect light and having an array of sensing locations, and collection optics arranged and configured to project light emanating from the sample platform onto the sensor. In typical operation, light from the targeted area is projected onto a first portion of the sensor comprising a first plurality of the sensing locations and light from proximal to the targeted area on the platform is projected onto a second portion of the sensor comprising a second plurality of the sensing locations, and a second signal detected by the second portion of the sensor is subtracted from a first signal detected by the first portion of the sensor to produce a background-reduced signal, e.g., a signal with reduced background related noise.

29 Claims, 4 Drawing Sheets

(58) Field of Classification Search
USPC .................. 348/241; 382/128, 129; 356/311; 250/208.1, 208.2
See application file for complete search history.

(56) References Cited

U.S. PATENT DOCUMENTS

| | | | |
|---|---|---|---|
| 7,286,232 B2 | 10/2007 | Bouzid | |
| 8,406,859 B2 * | 3/2013 | Zuzak | A61B 5/0071 257/440 |
| 2002/0158212 A1 * | 10/2002 | French | B01L 3/50853 250/459.1 |
| 2003/0078477 A1 * | 4/2003 | Kang | A61B 1/042 600/178 |
| 2005/0151972 A1 | 7/2005 | Boege et al. | |
| 2006/0119865 A1 * | 6/2006 | Hoyt | A61B 5/0059 356/625 |
| 2009/0245605 A1 * | 10/2009 | Levenson | A61B 5/0059 382/128 |
| 2009/0248367 A1 * | 10/2009 | Naya | G01J 3/0205 702/194 |
| 2010/0113940 A1 * | 5/2010 | Sen | A61B 5/0062 600/476 |
| 2012/0128264 A1 * | 5/2012 | Yazdanfar | A61B 5/0059 382/274 |
| 2012/0326055 A1 * | 12/2012 | Wilson | A61B 5/0059 250/459.1 |

OTHER PUBLICATIONS

Hillman et al. "Laminar optical tomography: high-resolution 3D functional imaging of superficial tissues", Proc. SPIE 6143, Medical Imaging 2006: Physiology, Function, and Structure from Medical Images, 61431M (Mar. 13, 2006).*

E.M.C. Hillman et al., Laminar optical tomography: high-resolution 3D functional imaging of superficial tissues, Processing of SPIE, vol. 6143, 6143M, Mar. 13, 2006.

Rowe, Chris A., et al. "Array biosensor for simultaneous identification of bacterial, viral, and protein analytes." *Analytical Chemistry* 71.17 (1999): 3846-3852.

* cited by examiner

DIFFERENTIAL SCAN IMAGING SYSTEMS AND METHODS

CROSS-REFERENCES TO RELATED APPLICATIONS

This application is a Continuation of U.S. non-provisional application Ser. No. 13/084,371 filed on Apr. 11, 2011.

BACKGROUND

The present invention relates to optical imaging with reduced background, and more specifically to systems and methods for directly measuring the amount of background noise and removing it from the detected signal.

Optical imaging is becoming more and more the method of choice for many measurement applications that demand high sensitivity and quantification. Recent scientific advances benefit from reliably detecting small and/or weak targets. In order to obtain reliable representations of such targets, it is desirable to use an imaging system that has low noise levels. Fluorescence imaging is one of the techniques that have significant capabilities to reliably achieve sensitive, quantitative measurements. With fluorescence imaging, the target to be imaged is illuminated by an optical signal having a first spectral content (excitation light), and a portion of such a signal is absorbed by at least part of the target and is re-emitted as an optical signal of a second spectral content (emission light). The emission light is then detected by a detection system as a measure of the properties of the target.

A fluorescence imaging system typically includes one or more sources and components that generate and deliver the excitation light to the target area. The system also includes components to collect light from the target area, separate the emission light from the excitation light, and deliver it to an optical sensor. One common method for separating the emission light from reflected and/or scattered excitation light is optical filtering. Various other methods are also used to achieve similar results. However, with all the techniques known to date, it is often difficult to completely prevent reflected and/or scattered excitation light from reaching the sensor. This adds an amount of non-fluorescence signal to the emission signal which, in turn, results in a non-accurate measurement of target properties such as quantity of fluorescence material. This is one type of optical background noise. Another known type of optical background is auto-fluorescence which results from non-target elements in the system absorbing a portion of the excitation light and re-emitting it as fluorescence, a portion of its content being within the second spectral range. Examples of components that can generate auto-fluorescence background noise include the media where the target resides, optical filters, and lenses. Yet another source of optical background noise is light generated by sources other than the excitation light sources that makes its way towards the sensor. There are also a number of other non-optical background sources, such as dark signals generated by the sensor itself and the electronics that drive it. They, too, cause an increase in the background noise and if not eliminated or reduced, limit the performance of the imaging system.

There are a number of techniques and implementations for improving the sensitivity of fluorescence imaging systems (see, e.g., U.S. Pat. No. 6,921,908; U.S. Pat. No. 6,495,812; U.S. Pat. No. 7,286,232; and U.S. patent application Ser. No. 12/785,308, the contents of each of which are hereby incorporated by reference for all purposes). These techniques range from hardware configurations to software processing of acquired images. Methods that rely more on hardware techniques are often preferred because they aim at the root-cause of the problems not at their symptoms. Within the hardware solutions, the most efficient are those that leverage any differences between the optical properties of target fluorescence emission and background noise to favorably select the former. And, as is well known in the optical imaging industry, techniques that work best for one type of background noise may not work well for others. There are also techniques that address more than one type of background noise in one design, but there still is a need for a more general way to eliminate or reduce the background noise irrespective of its origin or type.

Therefore it is desirable to provide systems and methods that overcome the above and other problems.

BRIEF SUMMARY

The present invention provides systems and methods for reducing or eliminating background related noise in optical imaging signals, and particularly to systems and methods for producing background-reduced fluorescence imaging signals.

Embodiments relate generally to optical imaging with reduced background, and more specifically to systems and methods for directly measuring the amount of background noise and removing it from the detected signal. The systems and methods are particularly applicable to optical scanning where background noise has a wider spatial extent than the desired signal. Examples of such background noise sources include detector dark signals, electronics noise, and light emissions that originate from areas other than target location(s) such as ambient lighting, scattering, and auto-fluorescence.

Various embodiments offer simple, but efficient methods for obtaining a good estimate of the total background portion of a detected signal and removing the background to obtain an improved, background-reduced signal with better sensitivity due to the removal of all or a portion of the background signal.

The details of the various embodiments are described in the following in reference to the application of fluorescence imaging by scanning First, examples are described of how to implement the techniques of the various embodiments in the most common fluorescence scanning techniques, namely point-scanning and line-scanning. Then, line-scanning with angular illumination is described in more detail. It is shown that an already sensitive scanning technique is rendered more sensitive by significantly reducing its residual background using techniques as disclosed herein.

According to one aspect of the present invention, an imaging system is provided that typically includes a sample platform and an illumination and detection system. The illumination and detection system typically includes an illumination system that provides illumination light from an illumination source to a targeted area on the sample platform, a sensor adapted to detect light and having an array of sensing locations, and collection optics arranged and configured to project light emanating from the sample platform onto the sensor. In typical operation, light from the targeted area is projected onto a first portion of the sensor comprising a first plurality of the sensing locations and light from proximal to the targeted area on the platform is projected onto a second portion of the sensor comprising a second plurality of the sensing locations, and a second signal detected by the second portion of the sensor is subtracted from a first signal detected by the first portion of the sensor to produce a background-reduced signal, e.g., a signal with reduced background related noise. In certain aspects, the sensor includes a plurality of sensor elements, each element defining one or more of the sensing locations. In certain aspects, the sensor includes a single sensor element having a plurality of sensing locations arranged in an array.

According to another aspect of the present invention, an imaging method is provided that typically includes illuminating a targeted area of a sample platform with illumination light, and imaging light emanating from the sample platform onto a sensor having an array of sensing locations, wherein light from the targeted area is projected onto a first portion of the sensor comprising a first plurality of the sensing locations and light from proximal to the targeted area on the platform is projected onto a second portion of the sensor comprising a second plurality of the sensing locations. The method further typically includes subtracting a second signal generated by the second portion of the sensor from a first signal generated by the first portion of the sensor to produce a background-reduced signal. In certain aspects, the sensor includes a plurality of sensor elements, each element defining one or more of the sensing locations. In certain aspects, the sensor includes a single sensor element having a plurality of sensing locations arranged in an array. In certain aspects, subtracting is performed in an intelligence module communicably coupled with the sensor or during readout from the sensor readout circuitry communicably coupled with the sensor. In certain aspects, the method further includes scanning the targeted area over the sample platform so as to build up an image of a sample on the sample platform over time. Scanning may include moving the sample platform relative to a fixed illumination and detection system, or moving an illumination and detection system relative to a fixed sample platform, or scanning the illumination across the sample platform with a fixed detection system and platform.

The various embodiments herein are also applicable in measurement systems having one or more types of background signals that reach a first target signal sensor together with other places within the system where only a small portion of the target signal reaches and where a second sensor can be placed to generate a measure of the background signal. The signal obtained by the second sensor is then removed from the first sensor to obtain low-background target signal.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1A illustrates the system in reflection mode and FIG. 1B illustrates the system in transmission mode.

FIG. 3A illustrates the system in reflection mode and FIG. 3B illustrates the system in transmission mode.

DETAILED DESCRIPTION OF THE INVENTION

The present invention provides systems and methods for reducing or eliminating background-related noise in optical imaging signals, and particularly fluorescence imaging signals.

Differential Scanning with Coaxial Illumination

Figure 1A:
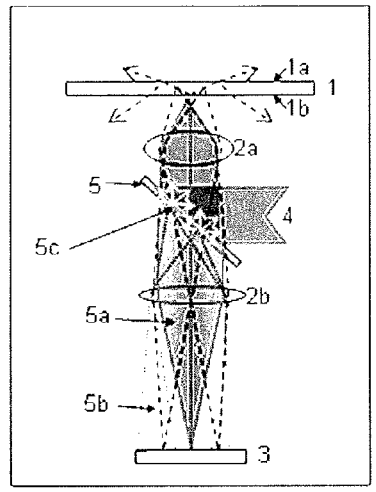
FIGS. 1A-B illustrate a fluorescence scanning system configuration according to one embodiment using coaxial illumination.

One type of fluorescence scanning system configuration is depicted by FIG. 1A. One or more fluorescently labeled targets are mounted on a platform 1 such as a glass plate, membrane coated slide, or other transparent, semi-transparent, and/or opaque media. A target area on the platform is illuminated by excitation light 4 which can be generated from laser source(s), LEDs, or broadband lamps and collected with some optical elements. The illumination light is typically filtered out using optical filters, dispersive elements, and the like to restrict the spectral content that arrives at the target plane, for example to excite only one of more than one fluorescence labels in the target plane. The fluorescence labels absorb a portion of the excitation light and the fluorescence emission is then collected through part of the detection system 2a and focused by another part of the detection system 2b onto a detector or sensor 3. One key aspect of this scanning method is that the excitation light and the collected emission light share part of the optical system, i.e. they are coaxial at the target plane. The paths are combined using, typically, a dichroic filter element 5 that reflects excitation light 4 towards the target 1 and transmits the emission light 5a towards the sensor 3. Another useful set-up includes a dichroic element 5 that transmits excitation light 4 towards the target 1 and reflects emission light 5a towards the sensor 3. Dichroic element 5 is typically mounted at an angle, for example 45°, in order to allow for mounting the source optics and sensor optics independently.

Other components necessary for detecting fluorescence are not included in FIG. 1A, but should be obvious to skilled in the art to recognize them and ways they can be included. One of such elements is emission filters. These are typically needed to block most of the excitation light that reflects off of the target area and allows emission light to reach the sensor. These can include more than one type of filter. For example, a notch filter to block most of the emission light and a band-pass filter to further block any residual excitation light leaking through the notch filter and further distinguish the desired emission light from other non-desired light. U.S.

Pat. No. 7,286,232, which is incorporated by reference in its entirety, discusses various aspects of useful imaging optics. So, FIG. 1A is to be interpreted as an indication of the coaxial nature of excitation and emission light paths and point out some of the sources of background noise addressed herein.

It is further assumed that FIG. 1A refers to cases where the illumination pattern in the target area is a point, a number of points, a line, or number of lines and the sample platform and/or the optical system are scanned in one or both directions to build up an image of larger area. For example, scanning can be achieved by moving the illumination light across the target area while the detection system and the target sample remain fixed. This can be done by a scanning mirror, for example, that sequentially aims the illumination beam at different locations over time and the detection system is accordingly aimed at those locations. As another example, scanning can be achieved by moving the sample platform relative to a fixed illumination and detection system, or by moving both the illumination and detection systems while holding the sample platform fixed.

Figure 1B:
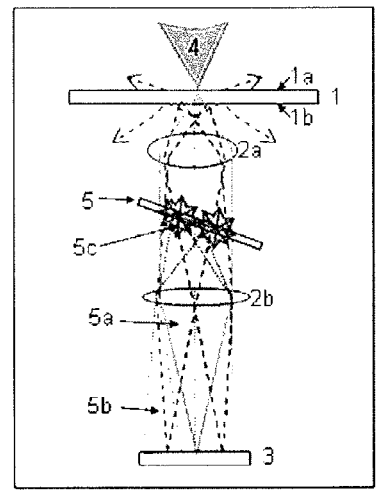

FIG. 1B is another example of coaxial illumination system, but in transmission mode instead of reflection mode as shown in FIG. 1A. This is also a common mode of imaging and can have various types of illumination patterns and additional elements as in the case of FIG. 1A. In this transmission mode, the target area of the platform (transparent or semi-transparent) is illuminated by excitation light 4, which impinges on the platform 1 from the backside of the platform relative to the optical detection system. Light 4 can be generated from laser source(s), LEDs, or broadband lamps. A combining dichroic element is typically not needed and element 5 shown in FIG. 1B refers to a blocking filter function, such as by a notch filter, that blocks most of the illumination light that passes through the target area. The blocking element 5 can be mounted at any angle, for example 8°, sufficient for its reflection to end up far enough from the field of view of the sensor and thus avoid any significant ghost reflections.

Both FIGS. 1A and 1B show two areas where optical background noise is typically generated and reaches the sensor. These are labeled as 5b and 5c. The former can be a result of part of the excitation light that bounces around in the vicinity of the target area and ends up generating some fluorescence light from the mounting media (auto-fluorescence) and any non-specific binding. This is more significant for membrane mounted targets where the membrane generates some auto-fluorescence and diffuses light around to cover an area wider than the desired target size. In addition, mounting media such as membranes diffuse part of the fluorescence light emitted from the target area itself in a similar manner. This results in some optical signal reaching the sensor and typically covers a wide area that includes the target image. Because of its diffusion and the variations in its origins, optical background 5b usually results in a relatively small, non-localized, background signal detected by the sensor.

Another area where optical background can be generated is in the optical elements such as in dichroic elements or blocking filters 5. This is mainly a result of the relatively high power of illumination light used, which causes auto-fluorescence emission 5c in the materials of such filters and optical elements in its path. Signal 5c can also include portions of illumination light that scatters off impurity particles or dust particles and end up leaking through to the sensor. In a manner similar to background light 5b, this also results in weak signal broadly distributed over the sensor area. Yet another source of optical background can be a leakage from ambient light or from other light sources within the system. Here, too, because of their locations relative to the sensor, any leakage is most likely to be predominantly non-localized and covers a large area of the sensor that includes the image of the target.

Figure 2A:
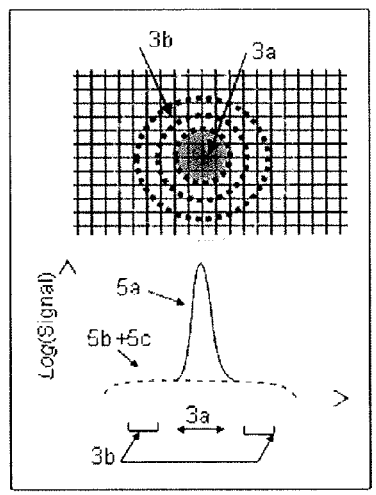
FIGS. 2A and 2B show typical patterns that target emission light and background light make at the sensor area for the cases of point-scanning and line-scanning, respectively, of the configurations shown in FIG. 1.
Figure 2B:
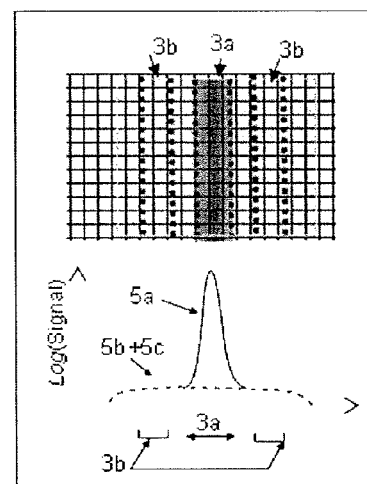

FIGS. 2A and 2B show typical patterns that target emission light 5a and background light 5b and 5c make at the sensor area for the cases of point-scanning and line-scanning, respectively. The fluorescence originating from the target area 5a, when in focus, is typically focused to a localized area that forms the image of the target. However, background light 5b and 5c and any other light leakage reach the sensor spread over a wider area that includes the area where signal 5a reaches but also includes another portion of the sensor where there is little light from signal 5a. In certain aspects this difference between desired fluorescence light 5a and undesired background light (5b+5c) is leveraged. If the portion of the sensor area where most of 5a and a portion of (5b+5c) reach and another portion of the sensor area where a minimum amount of 5a reaches but a similar amount of (5b+5c) reaches are detected separately, the following two readings are obtained:

$$S_1 = S + B$$

$$S_2 \approx B,$$

where B is background signal.

If the sensor areas are selected so that the second reading $S_2$ is comparable to the 'B' component of $S_1$, then the actual signal S can easily be obtained by subtracting $S_2$ from $S_1$. This subtraction can be accomplished directly through readout circuitry or in post measurement calculations. The latter can be accomplished with minimal additions of noise by applying a low-pass filter onto $S_2$ to eliminate the high frequency shot noise typically present with most detectors and thus the subtraction step does not add any to the measurement of $S_1$, i.e., the resultant noise in S is comparable to the noise present in $S_1$, which is the desired outcome.

Various types of sensor configurations can be used to accomplish this "Signal-Background" difference measurement. One typical type of sensors that lends itself easily to such an operation is an array sensor such as a CCD sensor or a CMOS sensor (FIGS. 2A and 2B).

An array sensor can be configured so that one or more of its elements 3a read $S_1$ and one or more of its other elements 3b read $S_2$. For CCDs, the subtraction can be easily performed post detection and for CMOS, it can also be performed through the readout circuitry.

Differential Scanning with Angular Illumination

Figure 3A:
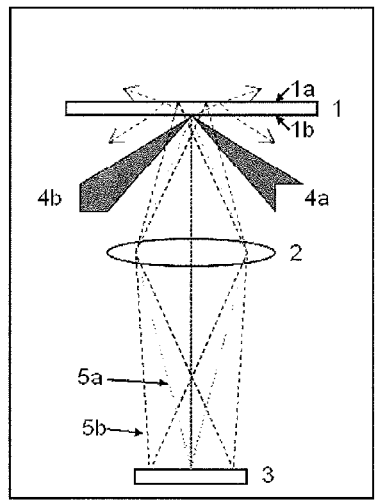
FIGS. 3A-B illustrate a fluorescence scanning system configuration according to one embodiment using angled illumination.
Figure 3B:
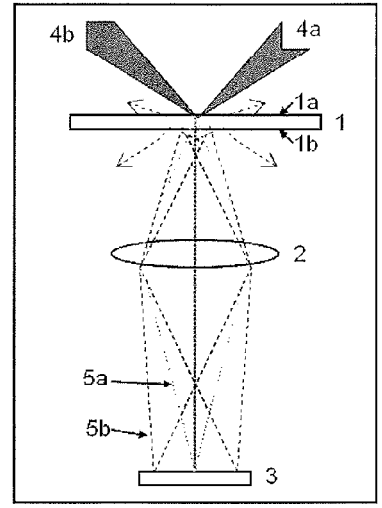
Figure 4A:
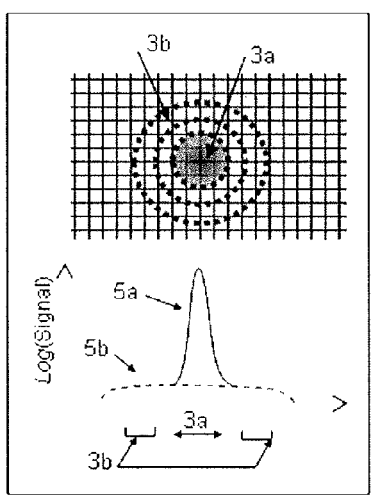
FIGS. 4A and 4B show typical patterns that target emission light and background light make at the sensor area for the cases of point-scanning and line-scanning, respectively, of the configurations shown in FIGS. 3A and 3B.
Figure 4B:
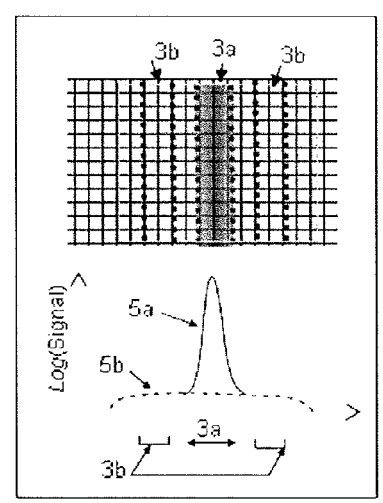

Another type of fluorescence scanning is depicted in FIGS. 3A and 3B. Here, too, detection can be in reflection mode (FIG. 3A) or in transmission mode (FIG. 3B) and the illumination pattern can be in the form of one or more spots or lines. This method differs from those depicted by FIGS. 1A and 1B, and described above, in that the illumination 4a impinges onto the target area at an angle, either from the front side (reflection mode) or the backside (transmission mode). Typical angles of incidences can range from a few degrees to more than 45°. The selection of the optimum angle is a trade-off between available working distances and positional sensitivities along the optical axis. FIGS. 4A and 4B, like FIGS. 2A and 2B, show typical patterns that target emission light 5a and background light 5b make at the sensor area for the common cases of point-scanning and line-scanning, respectively.

Angling the illumination offers the advantage of reflecting any of the specular reflections away from the detection collection optics and thus produces a much reduced optical signal to block by filters which, in turn, results in reduced background levels registered by the sensor. Another advantage is that excitation light does not pass through components in the emission path and thus there are less chances of generating auto-fluorescence 5c. The main contributor to the optical background signal in this case is from the target mounting medium, i.e. signal 5b. Applying the differential measurement method described above can eliminate or reduce this background significantly.

Differential Line Scanning with Angular Illumination

Figure 5:
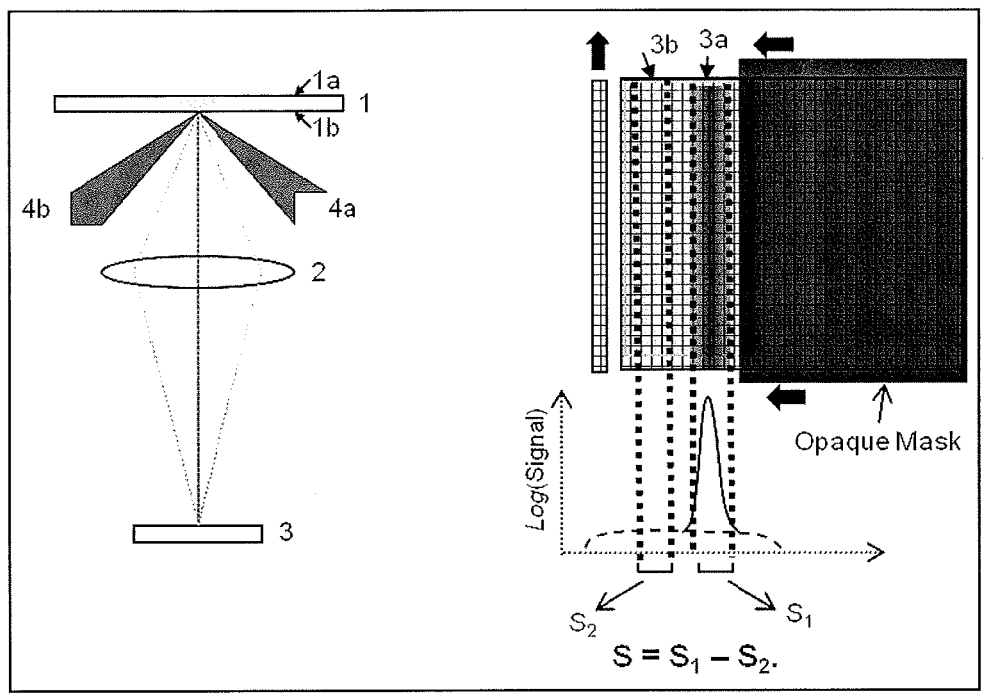
FIG. 5 illustrates laser line scanning and array detection with angular illumination (in reflection mode) according to one embodiment.

Another embodiment of the invention follows the angular illumination method of FIG. 3A and is shown in FIG. 5 where laser line scanning and array detection, e.g., CCD array detection, are used. An excitation laser beam 4a is incident on a target surface 1b at an angle of incidence such that most of the specular reflections 4b miss the fluorescence collecting optics 2. The laser light is preferably shaped to focus on a line perpendicular to the plane of incidence. It is preferable that such illuminating line be substantially uniform along its length and narrow in the other direction, for example diffraction-limited. The laser line excites fluorescently-labeled target areas which are then imaged onto a CCD array or other array. Such a detector array should be chosen with low dark current and read-noise so that any dark background is minimal. In addition, a CCD array readily allows for binning multiple pixels together to build up the "$S_1$=Signal+Background" and "$S_2$=Background" signals relatively independently. For example, with a CCD having a pixel size of 6.45 μm oriented so that the laser line is along the direction of its rows, $S_1$ and $S_2$ can be obtained by binning 10 rows each, i.e. rows 3a and 3b, respectively. The differential measure of the amount of fluorescence present is then obtained by subtracting $S_2$ from $S_1$.

With this embodiment, a target area is imaged by scanning the target sample 1 and/or the optical system in one or both directions. At each scanning position, two line images are obtained: One image by binning one or more rows around the image of the laser line location and another image by binning one or more rows away from the image of laser line location. These are designated in FIG. 5 as $S_1$ and $S_2$, respectively. In certain embodiments, an opaque mask can be used as shown to facilitate image collection with reduced background.

An example of a useful low-noise CCD is the Sony ICX285AL sensor chip. This chip is an interline type, where photo-generated charges are transferred row by row towards the output register which is then read-out serially. One or more rows can be added together (binned) at the output register before they're read out and the result is a row of signals that can represent the image of one line. The ICX285AL is capable of binning rows together with minimal additional noise when cooled. Cooling requirements are set by the maximum number of rows to bin and the longest exposure time per each line image. For example, 0° C. cooling with the ICX285AL produces minimal dark current for exposures less than 50 ms and binning up to 20 rows each. It is also beneficial to mask off the portion of the CCD that is away from the 3a and 3b regions in order to prevent any stray light from registering signals on the CCD and adding to the offset of the background. Even with these precautions, it may be inevitable that some residual dark or stray light signals gets registered as an offset on CCD pixels. But because these offsets are typically spatially broad in nature, they produce comparable offset registrations in regions 3a and 3b. Therefore, they form an addition to the optical background signals coming from the target medium and/or the optical elements in the system (signals 5b and/or 5c).

One skilled in the art will understand that other types of sensors and arrays of sensors, such as other CCD and CMOS sensors, can be used to accomplish the differential read described above. Additionally, one or more of the same or different sensors may be used, e.g., a single CCD or an array of CCDs or a single CMOS or an array of CMOS sensors. Other useful sensors might include photodiodes, avalanche photodiodes (APDs), silicon photomultiplier devices, an array of photomultiplier tubes, a focal plane array, etc.

Figure 6:
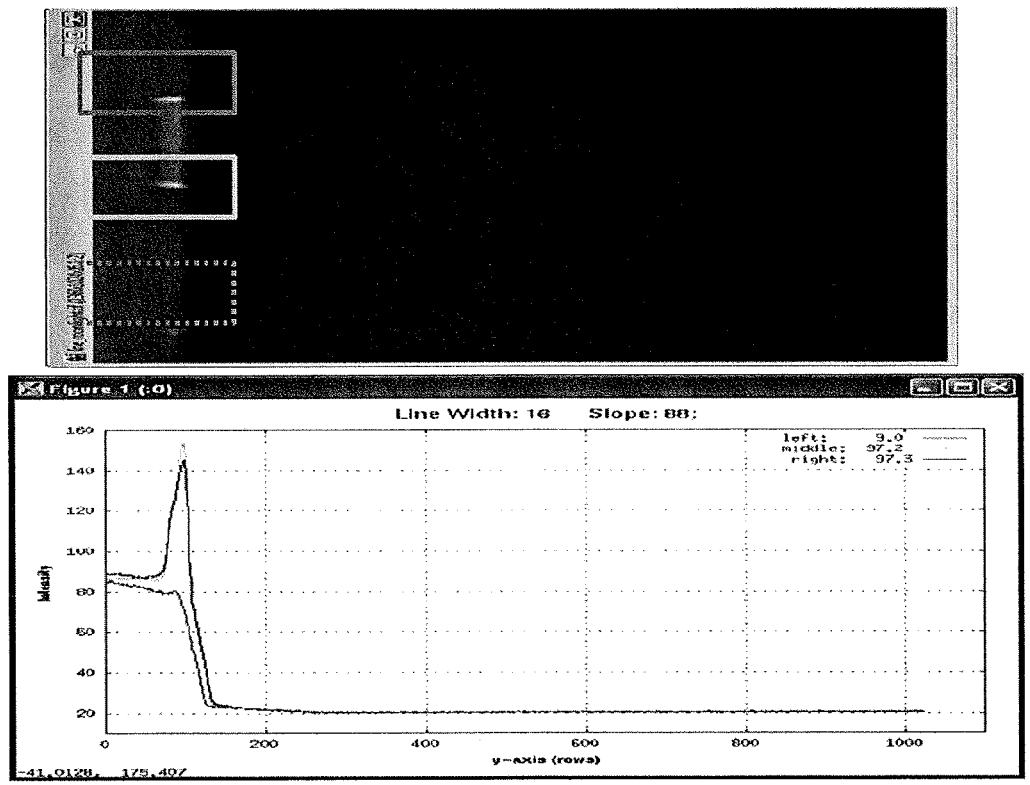
FIG. 6 shows one example of the CCD frames obtained at one scan position for the embodiment shown in FIG. 5, and three-plot cross-sections indicated by the top (left), center (middle), and bottom (right) rectangles on the image.
Figure 7:
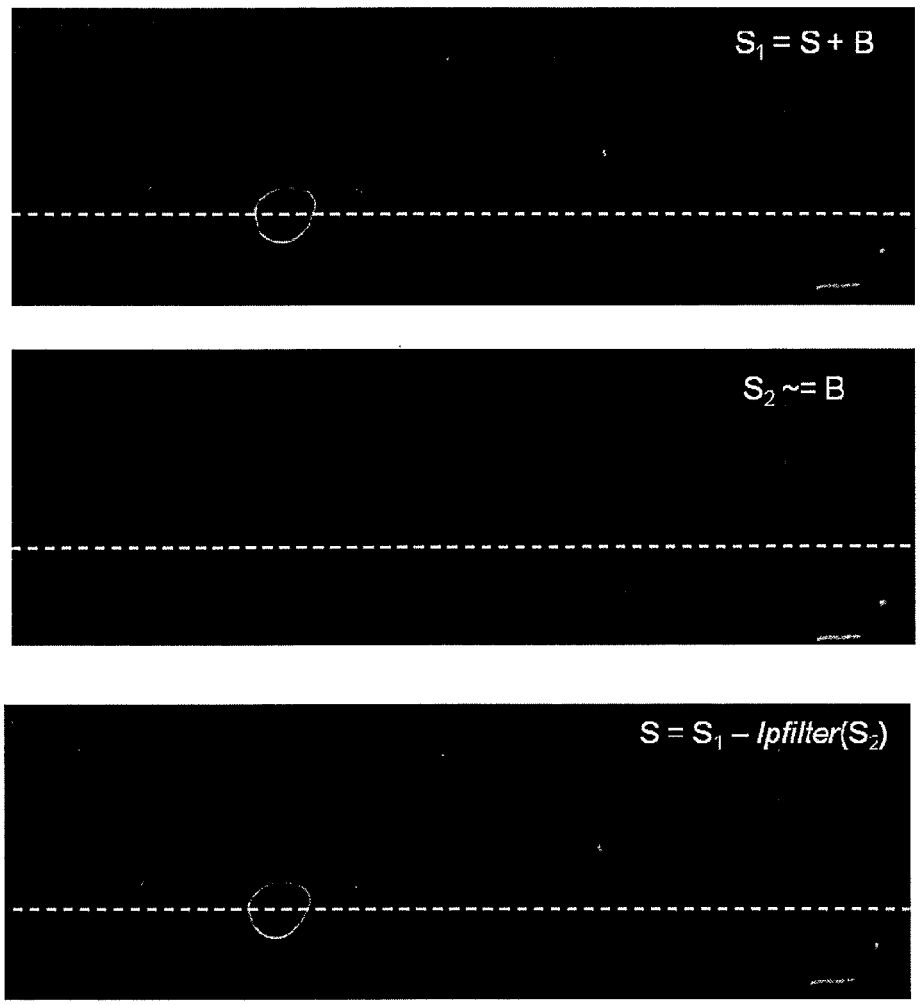
FIG. 7 shows the two scans obtained with the differential scanner S1 and S2 along with the calculated differential scan S. Also shown in FIG. 7 are 3 cross-section plots at the dashed lines across the three images.
Figure 7:
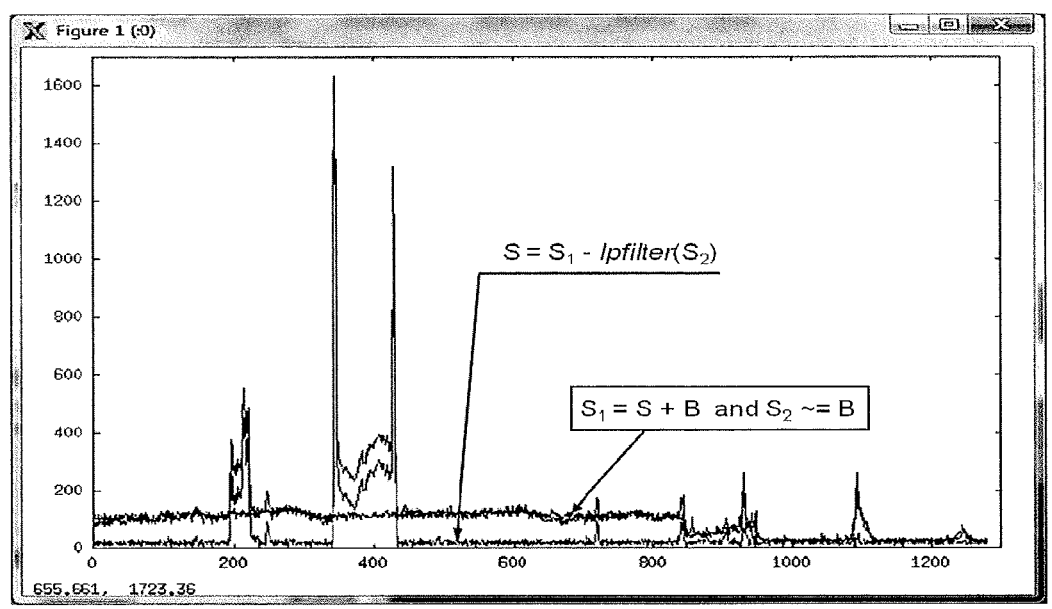

The result of a scan is two images: One image of the fluorescence target area that includes any background present, $S_1$, and another image that consists primarily of background, $S_2$. The latter is preferably filtered with a low-pass filter to reduce its read-noise and then subtracted from the former. The differential scan image is therefore obtained by $$S = S_1 - \text{lpfilter}(S_2)$$

Where lpfilter( ) is a low-pass filter function applied to the background image $S_2$. Other forms of filtering or other data processing would work equally well. FIG. 6 shows one example of the CCD frames obtained at one scan position according to one embodiment. The sample is positioned so that the laser line illumination crosses a fluorescently labeled spot about 2 mm in diameter. The display of the image is enhanced to show the residual background signal in the neighborhood of the line cross-section of the spot and clearly indicates that the background signal extends beyond the image of the line and is relatively constant across a number of rows. FIG. 6 also shows a three-plot cross-sections indicated by the top (left), center (middle), and bottom (right) rectangles on the image. The x-axis for the plots is CCD row numbers and the y-axis is signal level. The plots give an indication of the level of background signal and spot fluorescence. FIG. 7 shows the two scans obtained with the differential scanner $S_1$ and $S_2$ along with the calculated differential scan S. Also shown in FIG. 7 are 3 cross-section plots at the dashed lines across the three images. They show the level of background signal in each of scans $S_1$ and $S_2$ and the resulting minimum background level in the resulting differential scan.

Imaging by differential scanning according to the present embodiments advantageously relaxes the requirements for enclosure light tightness. Any residual optical background resulting from ambient lighting is automatically reduced or removed and the result is a background-free or background-reduced image. Also, differential scanning produces effects similar to confocal imaging. Light originating from out of focus areas produce spatially broad patterns at the sensor, i.e., relatively constant over the areas where both $S_1$ and $S_2$ are measured. This means that a differential scanning measurement will remove most of the out of focus background and produces "confocal-like" images.

In certain embodiments, scanning can include a third dimension (x, y and z) to obtain background-reduced two-dimensional images (x, y) at different depths (z). These images obtained at different depths can be combined to produce background-reduced, confocal-like, three-dimensional images (e.g., a volume). For example, the targeted area is scanned over the sample platform so as to build up a two dimensional image of a sample on the sample platform at a first depth of focus, and then, one or more times, the depth of focus is adjusted and the targeted area is scanned over the sample platform so as to build up a two dimensional image of a sample on the sample platform at a different depth of focus. Thereafter the two dimensional images (any set of two or more of the acquired two-dimensional images) are combined to produce a background-reduced three-dimensional image. In such embodiments, a scanning mechanism includes a mechanism to adjust the depth of focus (perpendicular to plane of sample platform).

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An imaging system, comprising:
a sample platform; and
an illumination and detection system, including:
an illumination system that provides a beam of excitation light from a source to a target area on the sample platform;
a sensor adapted to detect light and having an array of sensing locations; and
one or more optical elements arranged and configured to image light emanating from the sample platform onto the sensor, wherein fluorescent light from a portion of the target area illuminated by the excitation light is imaged onto only a first portion of the sensor comprising a first plurality of the sensing locations and background light from proximal to the portion of the target area illuminated by the excitation light on the platform is simultaneously imaged onto only a second portion of the sensor comprising a second plurality of the sensing locations different from the first plurality of the sensing locations; and
a scanning mechanism configured to adjust a relative position of the sample platform and the illumination and detection system such that the portion of the target area illuminated by the excitation beam changes at each of a plurality of scan positions, and
wherein, at each scan position, a second signal detected by the second portion of the sensor is subtracted from a first signal simultaneously detected by the first portion of the sensor to produce a background-reduced signal for the scan position of the plurality of scan positions.

2. The system of claim 1, wherein the system is a fluorescence imaging system, wherein the target area includes a fluorescent material, wherein the beam of excitation light includes light having an excitation wavelength of the fluorescent material, and wherein the fluorescent light from the illuminated portion of the target area imaged onto the first portion of the sensor includes fluorescence emissions from the fluorescent material.

3. The system of claim 1, wherein the beam of excitation light and the fluorescent light from the target area projected onto the first portion of the sensor are coaxial at a plane defined by the sample platform.

4. The system of claim 1, wherein the beam of excitation light and the fluorescent light from the target area imaged onto the first portion of the sensor are not coaxial at a plane defined by the sample platform.

5. An imaging method, comprising:
illuminating a portion of a target area of a sample platform with a beam of excitation light;
imaging light emanating from the sample platform onto a sensor having an array of sensing locations, wherein fluorescent light from the portion of the target area illuminated by the beam of excitation light is imaged onto only a first portion of the sensor comprising a first plurality of the sensing locations and background light from proximal to the portion of the target area illuminated by the beam of excitation light on the platform is simultaneously imaged onto only a second portion of the sensor comprising a second plurality of the sensing locations different from the first plurality of the sensing locations;
adjusting a relative position of the sample platform and the beam of excitation light such that the portion of the target area illuminated by the beam of excitation light changes at each of a plurality of scan positions; and
subtracting, at each scan position, a second signal generated by the second portion of the sensor from a first signal simultaneously generated by the first portion of the sensor to produce a background-reduced signal for the scan position of the plurality of scan positions.

6. An imaging method, comprising:
illuminating a portion of a target area of a sample platform with a beam of excitation light;
imaging light emanating from the sample platform onto a sensor having an array of sensing locations, wherein light from the portion of the target area illuminated by the beam of excitation light is imaged onto only a first portion of the sensor comprising a first plurality of the sensing locations and light from proximal to the portion of the target area illuminated by the beam of excitation light on the platform is simultaneously imaged onto only a second portion of the sensor comprising a second plurality of the sensing locations different from the first plurality of the sensing locations;
adjusting a relative position of the sample platform and the beam of excitation light such that the portion of the target area illuminated by the beam of excitation light changes at each of a plurality of scan positions; and
subtracting, at each scan position, a second signal generated by the second portion of the sensor from a first signal simultaneously generated by the first portion of the sensor to produce a background-reduced signal for the scan position of the plurality of scan positions.

7. The method of claim 6, wherein the method is a fluorescence imaging method, wherein the target area includes a fluorescent material, wherein the beam of excitation light includes light having an excitation wavelength of the fluorescent material, and wherein the fluorescent light from the target area imaged onto the first portion of the sensor includes fluorescence emissions from the fluorescent material.

8. The system of claim 1, wherein the sensor includes a sensor element selected from the group consisting of a CCD array chip, a CMOS array chip, a plurality of CCD array chips, a plurality of CMOS array chips, one or a plurality of photodiodes, a focal plane array, and an array of photomultiplier devices.

9. The system of claim 1, wherein the sensor includes one or more of a CCD array chip, a CMOS array chip, a photomultiplier device, a photodiode, a plurality of photodiodes, and a focal plane array.

10. The system of claim 1, the system further including a mechanism to move one or both of the sample platform, and the illumination; and detection system such that the target area on the sample platform is scanned in one or both directions defining a plane of the sample platform.

11. The system of claim 10, wherein the system is one of a point scanning system wherein the portion of the target area illuminated by the excitation light includes one or more focused spots onto one or a plurality of sensing locations, or a line scanning system wherein the portion of the target area illuminated by the excitation light includes an extended linear array of the sensing locations.

12. The system of claim 1, wherein the beam of excitation light and the light from the target area projected onto the first portion of the sensor are coaxial at a plane defined by the sample platform.

13. The system of claim 1, wherein the beam of excitation light and the light from the target area imaged onto the first portion of the sensor are not coaxial at a plane defined by the sample platform.

14. The system of claim 1, wherein the illumination source includes a source selected from the group consisting of a laser, an LED and a broadband lamp.

15. The system of claim 1, wherein the illumination system includes a scanning mechanism that moves the beam of excitation light such that the target area on the sample platform is scanned in one or both directions defining a plane of the sample platform.

16. The system of claim 1, wherein at each of the plurality of scan positions, the first plurality of sensing locations and the second plurality of sensing locations making up the first portion of the sensor and the second portion of the sensor, respectively, comprise different sensing locations in the array of sensing locations than at a previous scan position.

17. The method of claim 6, wherein illuminating includes directing the beam of excitation light from a source onto the target area of the sample platform so that the beam of excitation light is substantially coaxial, at the sample platform, with the fluorescent light being imaged onto the sensor.

18. The method of claim 6, wherein subtracting is performed in an intelligence module communicably coupled with the sensor.

19. The method of claim 6, wherein subtracting is performed during readout from the sensor readout circuitry communicably coupled with the sensor.

20. The method of claim 6, further including generating an image of a sample on the sample platform using the background-reduced signals for each of the plurality of scan positions.

21. The method of claim 6, wherein the adjusting includes moving the sample platform relative to a a stationary beam of excitation light.

22. The method of claim 20, wherein the sample platform is stationary, and wherein scanning includes scanning the beam of excitation light across the sample platform.

23. The method of claim 6, wherein illuminating includes directing the beam of excitation light from a source onto the target area of the sample platform so that the beam of excitation light is substantially coaxial, at the sample platform, with the light being imaged onto the sensor.

24. The method of claim 6, wherein the method is a fluorescence imaging method, wherein the target area includes a fluorescent material, wherein the beam of excitation light includes light having an excitation wavelength of the fluorescent material, and wherein the light from the target area imaged onto the first portion of the sensor includes fluorescence emissions from the fluorescent material.

25. The method of claim 6, further comprising displaying a representation of the noise-reduced signal on an output or display device.

26. The method of claim 6, wherein the sensor includes one of a single sensor element having a plurality of sensing locations arranged in an array, or a plurality of sensor elements, each element defining one or more of the sensing locations.

27. The method of claim 6, wherein illuminating includes directing the beam of excitation light from a source onto the target area of the sample platform at an angle relative to a normal to a plane defined by the sample platform.

28. The method of claim 6, wherein the adjusting occurs at a first imaging depth of focus so as to build up a two dimensional image of a sample on the sample platform at the first imaging depth of focus; and
one or more times:
i) adjusting the first imaging depth of focus to a different depth of focus; and
ii) scanning the target area over the sample platform so as to build up a two dimensional image of a sample on the sample platform at the different depth of focus; and thereafter:
combining the two dimensional images to produce a three-dimensional image.

29. The method of claim 6, wherein at each of the plurality of scan positions, the first plurality of sensing locations and the second plurality of sensing locations making up the first portion of the sensor and the second portion of the sensor, respectively, comprise different sensing locations in the array of sensing locations than at a previous scan position.

* * * * *